United States Patent [19]
Ryser

[11] Patent Number: 6,116,079
[45] Date of Patent: Sep. 12, 2000

[54] LIQUID COPPER HYDROGEN SAMPLE PROBE

[75] Inventor: Gary H. Ryser, Taylorville, Utah

[73] Assignee: Asarco Incorporated, New York, N.Y.

[21] Appl. No.: 09/226,045

[22] Filed: Jan. 5, 1999

[51] Int. Cl.[7] .............................. G01N 7/10; B22D 11/16
[52] U.S. Cl. ........................... 73/19.07; 75/648; 75/384; 436/75; 436/144
[58] Field of Search .............................. 73/19.01, 19.07, 73/19.1, 19.12; 75/384, 648; 148/508; 136/75, 134, 144, 145

[56] References Cited

U.S. PATENT DOCUMENTS

| | | |
|---|---|---|
| 2,861,450 | 11/1958 | Ransley . |
| 3,199,977 | 8/1965 | Phillips et al. . |
| 4,290,823 | 9/1981 | Dompas ................................ 148/508 |
| 4,670,055 | 6/1987 | Koslowski . |
| 4,695,043 | 9/1987 | Winkelmann et al. . |
| 4,754,591 | 7/1988 | Kastelic et al. . |
| 4,783,057 | 11/1988 | Sullins . |
| 4,828,014 | 5/1989 | Moscoe et al. . |
| 4,907,440 | 3/1990 | Martin et al. ........................... 73/19.07 |
| 4,924,570 | 5/1990 | Mizrah et al. . |
| 4,951,929 | 8/1990 | Schwarz et al. . |
| 5,000,362 | 3/1991 | Foglio et al. . |
| 5,031,444 | 7/1991 | Doutre et al. ........................... 73/19.07 |
| 5,092,500 | 3/1992 | Weber et al. . |
| 5,100,035 | 3/1992 | Dunworth et al. . |
| 5,154,139 | 10/1992 | Johnson . |
| 5,158,217 | 10/1992 | Huminsky et al. . |
| 5,188,689 | 2/1993 | Dunworth et al. . |
| 5,243,801 | 9/1993 | Aiken et al. . |
| 5,292,366 | 3/1994 | Miceli . |
| 5,293,924 | 3/1994 | Hugens, Jr. et al. .................... 164/452 |
| 5,373,976 | 12/1994 | Rancoule et al. . |
| 5,518,931 | 5/1996 | Plessers ................................ 73/19.07 |
| 5,850,034 | 12/1998 | Hugens, Jr. ............................ 73/19.07 |

OTHER PUBLICATIONS

BOMEN Inc. AISCAN, In–Line Measurement of Hydrogen In Molten Aluminum.
"*Extractive Metallurgy of Copper*" by A.K. Biswas and W.G. Davenport, First edition, Chapter 17, pp. 336–368.
*Wire Journal,* Sep. 1974, pp. 118–132, Continuous Casting and Rolling of Copper Rod at the M.H. Olen Copper Refinery Uses No Wheel by John M.A. Dompas et al.

*Primary Examiner*—Daniel S. Larkin
*Attorney, Agent, or Firm*—DeLio & Peterson, LLC

[57] ABSTRACT

A method is disclosed for improving the making of metals such as steel and copper by using a molten metal gas measurement system to measure the gas content of the molten metal particularly $H_2$ content, and to controlling the metal making process based on the gas content value. The preferred gas analyzer comprises an improved long lasting immersion probe body and an analyzer wherein the probe body is immersed in the molten metal and a carrier gas is cycled through the probe and analyzer. The carrier gas entrains gases diffusing into or formed in the probe body and this gas mixture is electronically compared with a reference value to provide a measurement of the gases in the molten metal and the process is controlled based on the analyzer results. Another important use of the gas analyzer is in molten metal degassing operations such as used in the steel industry. The improved probe body is preferably made from refractory mortar which is formed into a paste mixture with water, molded, and cured to form the probe body product.

13 Claims, 1 Drawing Sheet

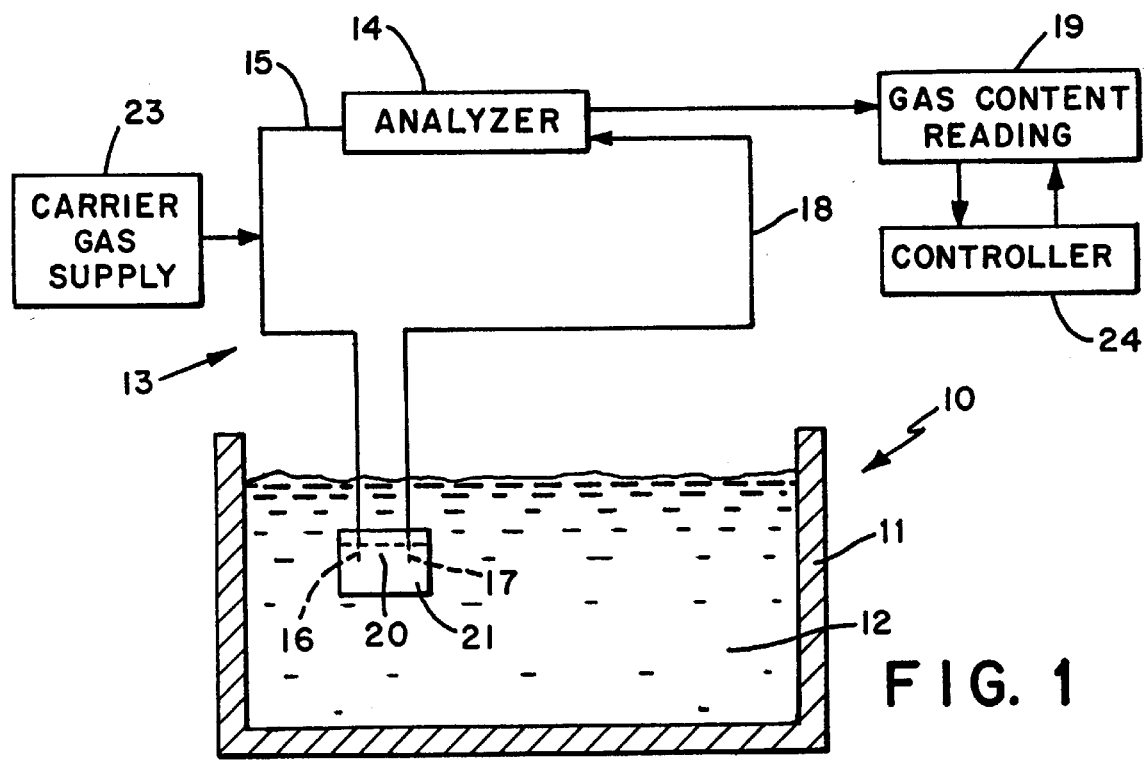
FIG. 1
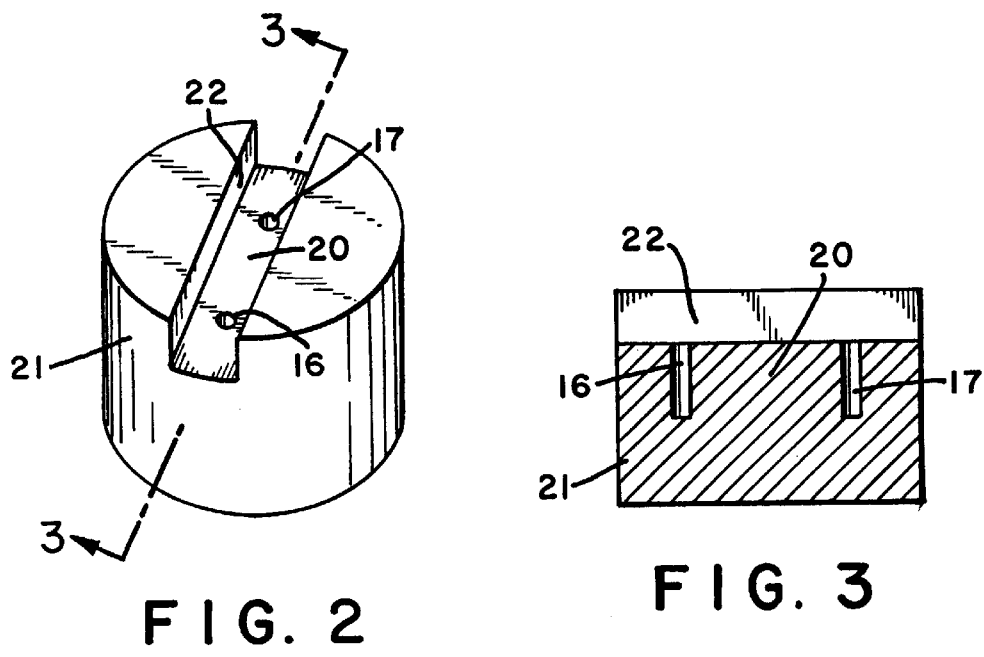
FIG. 2
FIG. 3

LIQUID COPPER HYDROGEN SAMPLE PROBE

BACKGROUND OF THE INVENTION

1. Field of the Invention

This invention relates to the making of a wide variety of metal products from molten metal using such processes as extraction of the metal from ore, purification processes, and mechanical working processes such as continuous casting and, more particularly, to improving the manufacturing method and the quality of the metal product, and in particular copper, by using an improved probe body in a gas measurement system used to measure the gas content of the molten metal during metal processing steps. The measurement system comprises an analyzer instrument and an improved long lasting probe body wherein the probe body is inserted into the molten metal at any of a number of process steps in the metal product making process and a carrier gas is cycled in a circuit between the analyzer instrument and the probe body with the analyzer electronically comparing a reference value with the value obtained by a mixture of the carrier gas and gases from the molten metal entrapped or formed in the probe body to provide a gas measurement content reading for the molten metal.

2. Description of Related Art

The production of metals such as steel involves a number of processing steps from extraction of iron from iron ore to the actual steel making step wherein molten iron is treated with oxygen and carbon to form the steel. In the steel making process and likewise in the copper making or other metal making processes, molten metals are processed and formed into a solid product. The manufacture of copper products by continuous casting is well-known in the art and the manufacturing process is described in the "Extractive Metallurgy of Coppers" by A. K. Biswas and W. G. Davenport, First edition, Chapter 17, pages 336–368, the disclosure of which is hereby incorporated by reference. The following description for convenience will be directed to the making of copper products although it will be appreciated by those skilled in the art that the method and apparatus of the invention may be used for other metal making processes where it is important to measure the gas content of the molten metal.

As described in Phillips et al., U.S. Pat. No. 3,199,977, which patent is hereby incorporated by reference, cathodes or other forms of pure copper are melted in a furnace and the molten copper fed to a holding furnace for casting. The Asarco shaft furnace is predominately employed and the copper is placed in the furnace at the top and is heated and melted as it descends down the shaft. The heat is provided by impinging and ascending combustion gases produced in burners near the bottom of the furnace.

The furnace is primarily a melting unit and the burners and combustion gases are such that the copper is generally not oxidized during melting. This is achieved by using specially designed burners which insure that unconsumed oxygen in the burner does not enter the furnace shaft and by controlling the fuel/air ratio of the burners to provide a slightly reducing atmosphere in the furnace. In general, the fuel/air ratio is controlled to provide a reducing flame having a hydrogen content of the combusted fuel of up to about 3% by volume, usually 1%–3%.

There is generally no holding capacity in the furnace bottom and the molten copper flows immediately into a separate burner fired holding furnace. In many installations, the launder connecting the shaft furnace and the holding furnace is also burner fired to likewise maintain the temperature of the copper and to minimize unwanted oxidation of the copper.

The molten copper in the holding furnace is then fed to a continuous caster, such as a Properzi or Southwire wheel caster or a Hazelett twin belt caster. In the Hazelett caster, molten copper is cast between two coincidentally moving steel belts and the casting, usually a bar shape, is fed directly into a rod-rolling mill. The rod is normally discharged into a pickling unit, coiled, and stored.

U.S. Pat. No. 4,290,823 granted to J. Dompas shows the basic continuous casting process for manufacturing copper and this patent is hereby incorporated by reference. The Dompas process produces an oxygen containing rod product which purportedly has the advantages of oxygen free copper (ductility) and the annealing capacity of tough pitch copper. The process uses a solid electrolyte containing an electrochemical cell to analyze the oxygen content of the molten copper in the holding furnace and adjusts the fuel/air ratio of the holding zone burners to maintain the desired oxygen level.

An article entitled Continuous Casting and Rolling of Copper Rod at the M. H. Olen Copper Refiner Uses No Wheel", by J. M. A. Dompas, J. G. Smets and J. R. Schoofs (Wire Journal, September 1974, pages 118–132) also shows a typical rod making process.

Regardless of the particular processes and controls used, the main concern is to enhance the quality of the final copper product and meet standards relating to appearance (surface quality), electrical conductivity, and physical behavior during fabrication and use. While various automatic mechanical type control techniques such as a surface quality detector are used in continuous casting systems, these techniques provide a relatively simple system for monitoring surface quality and do not control the more significant variables within the process directly or indirectly.

The same problems are encountered in making a wide variety of metals including steel and it is important to control operating parameters to provide a quality metal product. For example, hydrogen enbrittlement is a serious concern in steel manufacture and hydrogen control is very important in the steel making process. Degassing operations are an important process step in steel making and a reliable and efficient gas analyzer is essential for this purpose. Degassing may be performed using a wide variety of processes such as vacuum degassing, sparging the molten metal with an inert gas, such as nitrogen, or reacting the molten metal with a material that removes the unwanted gas, such as $H_2$. Regardless of the process used or parameters to be controlled, accurate gas measurement of the molten metal is essential for the process.

A number of gas measurement systems have been developed over the years. One gas measuring system which is particularly desirable uses a probe body immersed in molten metal to determine the concentration of the gas present in the metal as described in U.S. Pat. No. 4,907,440 to Martin et al., the disclosure of which is incorporated herein by reference. This gas measuring system comprises a combination of an immersion probe which consists of a gas-permeable, liquid-metal-impervious material of sufficient heat resistance to withstand immersion in the molten metal and an analyzer instrument. The probe body has a gas inlet to its interior and a gas outlet with the gas inlet and gas outlet being spaced from one another so that gas passing from the inlet to the outlet traverses a substantial portion of the probe body interior for entrainment of gas diffusing to the interior of the body from the molten metal. The probe body is immersed in the molten metal and a carrier gas circulated into the probe body to entrain gas that has diffused into the probe body from the molten metal. The carrier gas-entrained mixture is then passed through the outlet to an analyzer which measures the concentration of the entrained gas by electronic means. The gas measuring system is very effective for measuring the gas content of molten metal and a number of improvements have been made to the time to equilibrium and accuracy of the system particularly in the type carrier gas that is used to entrain the gas diffusing into the probe body from the molten metal.

A serious deficiency of the gas measuring system of Martin et al. however, is that the probe body is not very resistant to the deleterious effects of the molten metal. The probe body is damaged by the molten metal (e.g., disintegrates) and lasts for only a short time such as less than eight hours and often less than one hour when immersed in molten copper. The probe body must therefore be replaced frequently which is expensive and time consuming and which decreases the overall efficiency of the metal making process.

Bearing in mind the problems and deficiencies of the prior art, it is an object of the present invention to provide an improved method and gas analyzer system for measuring the gas content of molten metals, particularly hydrogen in molten copper and steel, which gas measurements may be used to control or monitor the various steps of a metal making process to control the gas of the molten metal.

It is a further object of the present invention to provide a long lasting probe body for use with a molten metal gas measurement system.

Another object of the invention is to provide an improved method for the making of long operating life probe bodies for use in molten metal gas measurement systems.

A further object of the invention is to the use of a gas analyzer system in molten metal operations including degassing operations to measure the gas content of the molten metal.

Another object of the invention is to make metals using the method and gas measurement system of the invention.

An additional object of the invention is to provide a gas analyzer system for measuring the gas content of molten metals.

Other objects and advantages of the present invention will become apparent from the following detailed description.

SUMMARY OF THE INVENTION

It has now been discovered that the method for making metals, and in particular steel and copper, from the step of separation of the metal from the ore or other sources to the final product made by the steps of continuous casting or other means, may be improved by using a molten metal gas measurement system comprising an analyzer instrument and an improved probe body wherein the probe body is inserted into the molten metal and a carrier gas is cycled in a circuit between the probe body and the analyzer unit and a comparative reading obtained between a reference value and the value obtained by a mixture of the carrier gas and gases diffusing into the probe body from the molten metal and/or formed in the probe body and which gases are entrained in the carrier gas. Gases entrained in the probe body are present in the molten metal and/or formed in the probe or at the probe interface. The gas reading is used to control parameters of the metal making process such as the fuel/air ratio of the burners employed in the melting furnace, launders, and/or holding furnace, in degassing operations and any other metal making steps where analyzing of the gas content of the molten metal may be employed.

A preferred gas measurement system as noted above is sold by Bomem Inc. under the name ALSCAN and its operation and use are fully described in U.S. Pat. No. 4,907,440, supra. The instrument comprises two units, the analyzer and the probe body, and was developed to measure the hydrogen content of liquid aluminum and related alloys. Other suitable probes and analyzers may be used such as the "Telegas" process described in U.S. Pat. No. 2,861,450 granted to Ransley et al. which is referred to in the '440 patent and which patent is hereby incorporated by reference. The Ransley probe is open at the bottom (such as an inverted bell) with the carrier gas being fed into the molten metal at the open area of the probe and being removed at the top thereof. For convenience, the following description will be directed to use of the ALSCAN instrument although other similar type instruments requiring an immersion probe may be used as will be appreciated by those skilled in the art.

Likewise, for convenience, the following description will be directed to the casting of copper although other molten copper and metal systems in particular steel and other metal making steps may suitably be analyzed using the gas measurement system of the invention. Broadly stated, the method for making copper or other metal by continuous casting or other means by measuring the gas content of a molten metal using a molten metal gas measurement system comprising an analyzer instrument and a probe body immersed in the molten metal comprises:

(a) melting copper or other metal in a furnace;

(b) preferably transferring the melted copper to a holding zone which is preferably heated;

(c) inserting into the molten copper a probe body comprising a gas-permeable, liquid-metal-impervious material of sufficient heat resistance to withstand immersion in the molten copper, said probe body having a gas inlet to its interior and a gas outlet therefrom the gas inlet and gas outlet being spaced from one another so that a carrier gas passing from the inlet to the outlet traverses a substantial portion of the probe body interior for entrainment of gas formed therein or at the probe interface and/or diffusing to the interior of the body from the molten metal, the probe body formed by casting in a mold a moldable paste or slurry of a particulate refractory material preferably a refractory mortar which is mixed with a fluid such as water and which paste hardens on curing and curing the molded paste to form a solid which is gas permeable and liquid-metal-impervious;

(d) comparing with an analyzer instrument by, e.g., electronic measuring means, the entrained gas and carrier gas mixture with a reference value or other measuring means, e.g., measuring the difference in resistivity of the entrained gas and carrier gas mixture and the reference value;

(e) determining the gas content of the molten metal and controlling the metal making process based on the gas content value, by, for example, adjusting, if necessary, the fuel/air ratio of one or more of the burners, the oxygen content of the molten copper or other operating parameters based on the analyzer results; and (f) repeating steps (c)–(e) during the metal making, e.g., casting operation.

In another aspect of the invention, the probe may be inserted into a molten metal, such as steel, and the gas content, predominately $H_2$, may be determined and this value used to control a degassing or other steel making operation.

In a further aspect of the invention, a probe body and a method for making a probe body for use in a gas measuring system for measuring the gas content of molten metals is provided comprising the steps of:

mixing a particulate refractory material preferably a refractory mortar with water to form a mixture preferably in the form of a stiff paste and which refractory material mixture hardens on curing to form a solid which is gas permeable and liquid-metal-impervious;

forming the refractory mixture into a desired probe body shape preferably including openings in the probe body to hold inlet and outlet gas conduit tubes which openings extend partially into the probe body and are spaced apart; and curing the formed mixture for an effective time and temperature to form the probe body.

In another aspect of the invention, the method of making the probe body comprises molding the refractory material mixture in an expendable mold which mold is burnt away during an elevated temperature curing process, e.g., sintering, leaving the probe body product.

In another aspect of the invention, the refractory material used to form the probe body is preferably a refractory mortar and the refractory material is selected from the group consisting of the carbides, nitrides and oxides of aluminum, magnesium, silicon, tungsten, and titanium. A preferred refractory mortar because of its demonstrated effectiveness comprises predominately silicon carbide, silicon dioxide (amorphous and crystalline), a mixture of hydrated alumina silicates, sodium silicate, and calcium lignosulfonate.

In another aspect of the invention, a gas analyzer apparatus is provided for the determination of the gas concentration of a molten metal, the apparatus comprising:

gas recirculation means for a carrier gas and a carrier gas-entrained gas mixture; an immersion probe having a gas inlet and a spaced apart gas outlet;

carrier gas supply means;

gas concentration determining means adapted to determine the proportion of the gas in the metal by comparatively measuring the carrier gas-entrained gas mixture with the carrier gas or other reference value; and conduit means connecting the carrier gas supply means, the gas inlet, the gas outlet, the gas recirculating means and the gas concentration determining means in a closed circuit;

wherein when the immersion probe is immersed in the molten metal, the carrier gas passing from the gas inlet to the gas outlet traverses a substantial portion of the probe body interior and entrains gas diffusing to the interior of the body from the molten metal, the probe body comprising a molded particulate refractory material which is gas-permeable and liquid-metal impervious.

The particulate refractory material is preferably a refractory mortar which is mixed with water to form a paste or slurry. As used in this specification, "refractory mortars" comprise finely ground dry refractory material which becomes plastic when mixed with water, is air or heat settable or curable, and is suitable for use in laying refractory brick of the type use in making the lining of furnaces such as those used in refining metal. A refractory mortar is generally comprised of at least one high temperature calcined refractory aggregate and at least one refractory powder which serves as a binder for the aggregate. Additional refractory aggregates and/or additional refractory powders may be used in various combinations. Where the binder does not provide sufficient cohesiveness, special binder materials may also be present. Also, special plasticizing materials may be present to improve the workability of the liquid mortar composition. The particle size of the refractory aggregates and refractory mortars is generally less than about 35 mesh preferably 70 mesh and finer. Refractory mortars of the type employed in the invention are commercially available and a preferred mortar is Carbofrax Mortar No. 8S sold by Saint-Gobain Industrial Ceramics and has a particle size of 70 mesh and finer, with about 30% having a particle size finer than 200 mesh.

In general, a refractory composition such as a refractory mortar when mixed with water forms a chemically-bonded dry refractory solid upon drying at room temperature. This refractory solid composition, heated at temperatures sufficiently high to fuse glass and the like, forms a ceramically-bonded refractory solid, which is the preferable form of the probe body of the invention.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 1 is a schematic diagram of an apparatus for measuring the gas content of a molten metal.

FIG. 2 is a perspective view of an immersion probe body of the invention.

FIG. 3 is a cross sectional view along lines 3—3 of FIG. 2.

DESCRIPTION OF THE PREFERRED EMBODIMENT(S)

In describing the preferred embodiment of the present invention, reference will be made herein to FIGS. 1–3 of the drawings in which like numerals refer to like features of the invention.

In general, the ALSCAN instrument relates the difference in electronic measurements between a reference value and a carrier gas-entrained gas mixture to the concentration of the gases in the molten metal and this value is outputted as an analyzer reading. As described in U.S. Pat. No. 4,907,440, the analyzer when used in molten aluminum measures the difference in resistivity of a bridge circuit which correlates this difference to the amount of hydrogen in the molten aluminum (see FIG. 2). As discussed in the patent, the difference in resistivity of the resistance wires is caused by, in effect, a difference in thermal conductivity of the entrained and carrier gas mixture and the reference gas. When hydrogen is present in the aluminum, the carrier gas (nitrogen)-entrained gas mixture thus contains hydrogen and the thermal conductivity is higher than the carrier gas alone and causes increased cooling of the wire, which difference is electronically measured and correlated. The comparison cell of the analyzer (catharometer) typically is open to the atmosphere since air is a suitable reference gas in the aluminum system when the carrier gas is nitrogen. The instrument may also be operated without a comparison cell by using a reference value instead of a reference gas, the reference value being the same value as if a reference gas were employed in the comparison cell.

When the instrument is used in a copper system, however, the resulting gas measurement curve when using nitrogen as the carrier gas does not resemble the curve for an aluminum bath, which is the subject of U.S. Pat. No. 5,293,924 assigned to the assignee of this invention.

When using the gas measurement system, control signals may be used to adjust process variables to control the process. For example, oxygen levels, adjusting of particular burners in the system, degassing, exposing the copper to other reducing or oxidizing agents, purging of the copper with neutral substances (nitrogen), temperature level, agitation of the melt to remove gases, etc. In operation, the probe body is inserted into the molten metal and gas measurement signals from the analyzer will be sent to a control unit based on the amount of gas in the molten metal. These values are used to control the process.

Referring now to FIG. 1, a schematic diagram of a gas measurement analyzer system is shown generally as 13 to demonstrate the gas measuring process of the invention. A molten metal system to be measured is shown generally as 10 and comprises a vessel or tank 11 holding a molten metal 12 containing gases therein. The analyzer system 13 comprises an analyzer unit 14, a gas probe inlet conduit 15, and a gas probe carrier gas-entrained gas mixture outlet conduit 18. A carrier gas supply 23 supplies carrier gas to the probe input conduit 15. Input conduit 15 communicates with inlet opening 16 in probe body 21. An outlet opening 17 in probe body 21 communicates with gas probe carrier gas-entrained gas mixture outlet conduit 18. Openings 16 and 17 in probe body 21 are separated by a space 20. This enables the carrier gas entering probe body 21 through conduit 15 and opening 16 to travel through probe body 21 and exit through opening 17 into conduit 18. Gas in the molten metal 12 diffuses into probe body 21 and is entrained with the carrier gas and exits as a carrier gas-entrained gas mixture through opening 17 into conduit 18 and into analyzer 14. A cycle is formed wherein at equilibrium a carrier gas-entrained gas mixture is flowing through conduit 15, probe 21, conduit 18, and analyzer 14. Based on the analyzer measuring system, a gas reading is obtained as output 19 and may be used by controller 24 to adjust operating parameters.

A preferred probe body 21 is shown in FIG. 2. The probe body 21 is cylindrical and has a channel 22 at the upper surface thereof. Openings 16 and 17 are shown which receive conduits 15 and 18 respectively (see FIG. 1) for the introduction of the carrier gas and the removal of a carrier gas-entrained mixture, respectively.

FIG. 3 is a cross sectional view of FIG. 2 and shows openings 16 and 17 extending partially into probe body 21. As can be seen, there is a space 20 between openings 16 and 17 to allow the carrier gas to travel across the probe body and to entrain gas in the molten metal which diffuses into the probe body 21.

The probe body 21 is preferably cylindrical although other shapes can be employed as shown in the Martin patent, supra. A preferred diameter is about 0.75 to 1.25 inch and a preferred height about 0.5 to 0.75 inch. The depth of the openings is up to about 20% to 50% or more of the height, preferably about 30% of the height and of a sufficient diameter to accommodate the inlet and outlet conduits, e.g., 0.05 to 0.1 inch, e.g., 0.065 inch. The slot is optional and is preferred for compatibility with existing gas measurement analyzer systems.

The preferred probe body as described in the '440 patent consists of a monolithic body of a gas-permeable, liquid-metal-impervious material having a desired porosity and pore size. The porosity is defined as the proportion of the total volume of the probe body that is occupied by the voids within the body and a suitable range is about 5% to about 80% or higher. The pore size can vary over a wide range usually about 0.5 micrometers to 2,000 micrometers or higher. Generally, tubes extend into the probe body, one tube for introducing the carrier gas and the other tube for transferring the carrier gas and, after immersion in the molten copper, entrained gases from the molten metal (and any gases formed which are within the probe body) are cycled to an analyzer which electronically measures and compares the carrier gas and the entrained gases mixture with a reference value. The analyzer computes an output which is used by control units to control the process. It will be understood that the term entrained gases include gases which are formed within the probe or at the probe-molten metal interface by individual gases existing in the molten metal combining (e.g., chemical reaction) due to the temperature, proximity of the gases in the probe, probe-melt interface reaction, etc.

In a typical preferred copper rod manufacturing operation and typical gas measurement cycle, the probe body will be flushed with the carrier gas from carrier gas supply 23 for a length of time to ensure that only the carrier gas remains in the circuit and the thermal conductivity of the carrier gas used to establish the reference value. Accordingly, the carrier gas is passed through the entire circuit entering at the probe gas inlet 16, exiting the porous probe body 21 and exiting the outlet 17 passing through line 18, analyzer 14, and line 15 back into probe 21. This procedure is continued until only the carrier gas remains in the circuit. The flushing is then stopped and the probe body immersed into the molten copper with the volume of carrier gas in the circuit being constantly circulated through the probe and the analyzer electrical measuring means. The pressure of the carrier gas in the circuit will quickly reach a steady value. Upon immersion, gases in the molten copper enter the porous probe body or are formed therein and the circulation of the carrier gas and entrained gas mixture is continued until substantial concentration equilibrium is reached. At the end of this period or continually over a time period, the analyzer takes a measurement of the electronic comparative difference between the reference value and entrained gases and carrier gas mixture and converts this difference into a gas content analyzer reading.

Flushing with the carrier gas can also be performed by passing the carrier gas into both the input 16 and outlet 17 with the carrier gas exiting the porous body 21. After flushing is completed, the flow of carrier gas is stopped and the probe inserted into the molten metal and the process as described above continued.

In a typical copper operation, the probe body is immersed in the molten metal and gas content readings obtained. If the gas content readings typically after equilibrium are at the desired set point, no changes are made to the process. If the gas content readings increase, the fuel/air ratios will be typically decreased to achieve the desired reading.

In other metal making operations, such as a degassing operation in a steel making process, the probe body is inserted into the molten steel (metal) and a carrier gas passed through the probe body and through the gas analyzer system. A gas content reading will be obtained which can be correlated to the hydrogen and other gas content of the molten steel and the degassing operations controlled based on this value. Vacuum, sparging, or chemical reaction may be used to control the degassing process based on the gas content value of the molten metal as described above. Other similar control procedures can be used with the gas measurement system of the invention.

As discussed fully in the '440 patent, the probe body of the preferred gas analyzer system consists of a probe body of typically chosen porosity, pore size, and permeability and is provided with a gas inlet and a gas outlet spaced sufficiently apart so that the circulating carrier gas traverses a substantial portion of the interior of the probe body.

The porosity of the probe body is usually expressed as a percentage and is simply the proportion of the total volume of the body that is occupied by the voids within the body. A highly porous body has a high percentage of voids. The range of porosity for the probe body of the invention is a minimum of about 5% and a maximum of about 80%, but preferably in the range of 20% to about 60%, and more preferably in the range of about 35% to about 40%.

The pore size of the probe body can vary over a wide range from about 0.5 micrometers to 2000 micrometers or more. For example, the size of the hydrogen molecule in the metal is in the order of $2 \times 10^{-4}$ micrometers and the gas can therefore easily diffuse into the probe body even in the smallest sized pores. The preferred pore size is in the range of 10 micrometers to 1,000 micrometers, and more preferably in the range of 50 micrometers to 200 micrometers.

Permeability is another important consideration in the material choice since a probe body of porosity and pore sizes within preferred ranges may still be unsatisfactory if the cells or voids are completely closed off from one another or are so poorly interconnected that the gases cannot mix together within a reasonable period of time. Permeability may be generally defined as the rate by which a gas or liquid will pass through a material under a specified difference of pressure. It is usually expressed in terms of Darcies. With the probe of the prior art, it is preferred that the permeability be in the range of about 2 to 2,000 Darcies, and preferably in the range of 10 to 100 Darcies.

It is further described in the '440 patent, that the pore size of the material be such that both the carrier gas and hydrogen diffuse readily so that they will become mixed with one another while it must be impossible for the metal to enter more than the surface layer of the probe body. Thus, it is usually found that at the conclusion of the gas measurement that a thin skin of solidified metal has mechanically adhered to the exterior surface of the probe. It is advantageous for the exterior surface of the probe body to be metal-wettable so as to sustain a high diffusion interface between the metal and the probe, but in practice it is disclosed that it has been found that reproducible results can be obtained with a monolithic body of non-wettable materials particularly if the probe and/or the metal are stirred. The presence of the above described thin skin of metal on the probe surface indicates that the surface has become wetted and once this has taken place the surface will remain wetted. Wetting could be facilitated by precoating the body with a thin layer of a suitable metal which may be applied by using any of the well known processes for application such as dipping, spraying, electrolytic, electrodes, etc., the layer being preferably of about 10 micrometers to 1,000 micrometers in thickness.

The coating can be a material that has a catalytic action towards the hydrogen or other gas being measured, promoting association from the monatomic state in the molten metal to the molecular diatomic state in the probe body for entrainment in the carrier gas. Particularly suitable materials are disclosed as platinum which can be readily deposited and can provide very thin layers of from commercial platinising solutions.

The shape of the probe body is disclosed in the Martin et al. '440 patent as not being critical, but it is preferred that in at least one dimension it be as small as practical to provide a corresponding minimum path length for the gas to diffuse into the block interior. Preference is also given to shapes to maximize active metal/probe surface area for a given probe volume. It has been found that wherever possible edges of the body are rounded so as to avoid as much as possible sharp corners that are particularly susceptible to mechanical shock. It is also disclosed that for a rectangular probe that the thickness of the probe to provide a desirable path length should be between about 0.2 inch and 0.6 inch with the minimum being determined by the strength of the material. Advantageously the volume for the rectangular probe is between 1 cc and 10 cc, preferably from 3 cc to about 5 cc. The preferred cylindrical probe of the invention is about 6 cc.

The probe body is also provided with two parallel bores which respectively receive the end of two tubes which provide inputting the carrier gas and removing the carrier gas entrained gas mixture. The tubes can be cemented in the probe body using a heat resistant cement.

The probe body of the invention when made as discussed hereinabove, is compatible with the Martin system and provides comparable gas content readings but at a much increased probe body operating life. The probes of the invention have an operating life in molten copper of typically greater than about twenty-four hours as compared to commercial probes which have an operating life of less than eight hours and often less than one hour.

The material used to make the probe is refractory in nature and able to withstand the temperature of immersion without softening to an acceptable degree provided that the probe meets on curing the combination of mechanical strength, porosity, pore size and permeability. Examples of the preferred particulate refractory materials are refractory mortars including carbides, nitrides and oxides of aluminum, magnesium, silicon, zirconium, tungsten, and titanium. The preferred refractory material because of its demonstrated effectiveness is a mixture of predominately silicon dioxide (amorphous and crystalline), a mixture of hydrated alumina silicate, sodium silicate, and calcium lignosulfonate. It is believed that the sodium silicate acts as the binder. A material having this composition is sold at Carbofrax Mortar No. 8S and is used for bonding refractory bricks together, such as for lining a furnace.

Broadly stated, to make the probe body of the invention, the above refractory mortar is mixed with water to form a mixture having preferably the consistency of a stiff paste such as putty. The paste is then formed into the desired probe shape and cured to form the probe body product. The shaped mixture is preferably first air dried and then heated (sintered) in an oven to form the final probe body product. The water to mortar ratio is about 45 cc water to one pound refractory mortar, and provides a stiff paste consistency which can be molded and formed into a solid product.

Various embodiments of the present invention may now be illustrated by references following the specific example. It is to be understood however that such examples are presented for purpose of illustration only and the present invention is in no way to be deemed as limited thereby.

EXAMPLE 1

A tube of acrylic plastic having a one inch outside diameter and ⅞ inch inside diameter was cut to a length (height) of ⅝ inch with a 3/32 inch deep×3/16 wide slot on the centerline at the upper end of the tube. Carbofrax Mortar No. 8S was mixed with water to make a stiff paste using about one pound Carbofrax Mortar mixed with 45 cc of water to form the stiff paste. The refractory mortar mixture is then placed in the tube and packed down so that there are substantially no voids in the molded mortar. A steel straight-edge is used to remove the excess mortar from the center slot that runs from side to side in the plastic tube. Two (2) 0.065 inch diameter holes are formed in the center slot 3/16 inch from each side of the plastic tube to a depth of 7/32 inch. The mortar paste mixture in the mold is left to stand for two hours at ambient temperature. The mortar paste mixture in the mold is then placed in an oven and fired at 1250° C. for twenty four hours. The acrylic plastic ashes in the oven leaving the probe body product.

Use of the above probe body in a gas measurement analyzing system for measuring hydrogen in molten copper as shown in FIG. 1 has an operating life of greater than about twenty four hours total immersion time in the molten copper. This is to be compared with a commercial probe body which generally lasts for less than 8 hours total immersion time and often less than one hour. The immersion probe of the invention also exhibited excellent gas measurement properties in the gas analyzer system.

EXAMPLE 2

An immersion probe was made in accordance with Example 1. The Carbofrax Mortar No. 8S was then screened to provide refractory material finer than 200 mesh (this fraction is about 30% of the refractory mortar). This fine material was then formed into a paste as in Example 1 and formed into an immersion probe as in Example 1. Carbon monoxide was then fed into the inlet of the probe and taken out of the outlet. The probe was standing in air and when equilibrium was established, a flame was used to ignite gas exiting from the probe body. The probe body made using the total refractory mortar mixture exhibited a blue uniform flame around the periphery of the probe showing that the CO was exiting the probe evenly. For the other probe, the flame was predominately at the top of the probe demonstrating the desirability of using the as-is mortar mixture. The example also demonstrates that the probe body when immersed in molten metal and under a molten metal hydrostatic head has gas transmission properties suitable for its use as a probe in a gas measurement system.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method for making copper or other metal by continuous casting by measuring the gas content of a molten metal using a molten metal gas measurement system comprising an analyzer instrument and a probe body comprises the steps of:

(a) melting metal in a furnace;

(b) inserting into the molten metal a probe body comprising a gas-permeable, liquid-metal-impervious material of sufficient heat resistance to withstand immersion in the molten metal, said probe body having a gas inlet to its interior and a gas outlet therefrom, the gas inlet and gas outlet being spaced from one another so that a carrier gas passing from the inlet to the outlet traverses a substantial portion of the probe body interior for entertainment of gas formed therein or at the probe interface and/or diffusing to the interior of the body from the molten metal, the probe body formed by casting in a mold a moldable paste or slurry of a particulate refractory mortar having a particle size less than about 35 mesh, the mortar containing a refractory material selected from the group consisting of carbides, nitrides and oxides of aluminum, magnesium, indium, tungsten and titanium and which paste hardens on curing and curing the molded paste by sintering to form a solid probe which is gas permeable and liquid-metal-impervious;

(c) comparing with an analyzer instrument the entrained gas and carrier gas mixture with a reference value;

(d) determining the gas content of the molten metal and controlling the metal making process based on the gas content value; and (e) repeating steps (b)–(d) during the metal making operation.

2. The method of claim 1 wherein the molten metal is copper.

3. The method of claim 1 wherein the molten metal is steel.

4. The method of claim 3 wherein the molten metal steel is degassed depending on the gas content of the molten steel.

5. A gas analyzer apparatus for the determination of the gas concentration of a molten metal, the apparatus comprising:

an immersion probe having a gas inlet and a spaced apart gas outlet;

carrier gas supply means;

gas recirculation means for the carrier gas and a carrier gas-entrained gas mixture;

gas concentration determining means adapted to determine the concentration of the gas in the metal by comparatively measuring the carrier gas-entrained gas mixture with the carrier gas or other reference value; and conduit means connecting the carrier gas supply means, the gas inlet, the gas outlet, the gas recirculating means, and the gas concentration determining means in a closed circuit;

wherein when the immersion probe is immersed in the molten metal, the carrier gas passing from the gas inlet to the gas outlet traverses a substantial portion of the probe body interior and entrains gas diffusing to the interior of the body from the molten metal, the probe body comprising a particulate refractory mortar having a particle size less than about 35 mesh which is mixed with a liquid to form a paste, molded to the desired shape and sintered and which probe is gas-permeable and liquid-metal-impervious.

6. The apparatus of claim 5 wherein the particulate refractory mortar contains a refractory material selected from the group consisting of carbides, nitrides, and oxides of aluminum, magnesium, silicon, tungsten, and titanium.

7. The apparatus of claim 6 wherein the immersion probe is cylindrical.

8. A method for making an immersion probe body for use in a gas measuring system for measuring the gas content of molten metals comprising the steps of:

mixing a particulate refractory mortar having a particle size less than about 35 mesh with liquid to form a mixture in the form of a stiff paste and which refractory mortar mixture hardens on curing to form a solid which is gas-permeable and liquid-metal-impervious;

forming the refractory mixture into a desired probe body shape; and curing by sintering the formed mixture for an effective time and temperature to form the probe body.

9. The method of claim 8 wherein the liquid is water.

10. The method of claim 9 wherein the particulate refractory mortar contains a refractory material selected from the group consisting of carbides, nitrides, and oxides of aluminum, magnesium, silicon, tungsten, and titanium.

11. The method of claim 8 wherein openings are provided in the probe body to hold inlet and outlet gas conduit tubes and which openings extend partially into the probe body and are spaced apart.

12. An immersion probe body made using the method of claim 10.

13. An immersion probe body made using the method of claim 11.

* * * * *